United States Patent
Elias et al.

(10) Patent No.: US 9,921,219 B2
(45) Date of Patent: Mar. 20, 2018

(54) BACTERIOPHAGE-BASED BIOSENSOR FOR MICROBIAL DETECTION

(71) Applicant: The Governors of the University of Alberta, Edmonton (CA)

(72) Inventors: Anastasia Elias, Edmonton (CA); Dominic Sauvageau, Edmonton (CA); Zachary Storms, Edmonton (CA); Chanchan Wang, Edmonton (CA); Preetam Anbukarasu, Edmonton (CA); Diana Martinez-Tobon, Edmonton (CA)

(73) Assignees: Anastasia Elias, Edmonton, Alberta (CA); Dominic Sauvageau, Edmonton, Alberta (CA); Zachary Storms, Edmonton, Alberta (CA); Chanchan Wang, Edmonton, Alberta (CA); Preetam Anbukarasu, Edmonton, Alberta (CA); Diana Martinez-Tobon, Edmonton, Alberta (CA)

( * ) Notice: Subject to any disclaimer, the term of this patent is extended or adjusted under 35 U.S.C. 154(b) by 55 days.

(21) Appl. No.: 14/837,621

(22) Filed: Aug. 27, 2015

(65) Prior Publication Data

US 2016/0061830 A1 Mar. 3, 2016

Related U.S. Application Data

(60) Provisional application No. 62/042,424, filed on Aug. 27, 2014.

(51) Int. Cl.
*C12Q 1/68* (2006.01)
*G01N 33/569* (2006.01)
*G01N 33/543* (2006.01)

(52) U.S. Cl.
CPC . *G01N 33/56911* (2013.01); *G01N 33/54373* (2013.01)

(58) Field of Classification Search
None
See application file for complete search history.

(56) References Cited

U.S. PATENT DOCUMENTS

| | | | |
|---|---|---|---|
| 6,174,990 B1 * | 1/2001 | Noda | C08J 5/18 428/913 |
| 7,625,556 B2 | 12/2009 | Sulakvelidze et al. | |
| 7,625,739 B2 | 12/2009 | Pasternack et al. | |
| 7,625,740 B2 | 12/2009 | Pasternack et al. | |
| 7,625,741 B2 | 12/2009 | Pasternack et al. | |
| 7,635,584 B2 | 12/2009 | Sulakvelidze et al. | |
| 7,674,467 B2 | 3/2010 | Sulakvelidze et al. | |
| 7,745,194 B2 | 6/2010 | Pasternack et al. | |
| 7,985,573 B2 * | 7/2011 | Yacoby | A61K 47/48238 424/93.2 |
| 8,003,323 B2 | 8/2011 | Morris et al. | |
| 8,685,696 B2 | 4/2014 | Pasternack et al. | |
| 8,685,697 B1 | 4/2014 | Pasternack et al. | |
| 8,956,628 B2 | 2/2015 | Mathers et al. | |
| 9,212,383 B2 | 12/2015 | Schofield | |
| 9,255,251 B2 | 2/2016 | Lipinski et al. | |
| 9,320,795 B2 | 4/2016 | Mathers et al. | |
| 9,404,089 B2 | 8/2016 | Mathers et al. | |
| 2013/0122549 A1 | 5/2013 | Lu et al. | |
| 2015/0004595 A1 | 1/2015 | Koeris et al. | |

FOREIGN PATENT DOCUMENTS

WO    WO 2014/163479    *    9/2014    ............... C12Q 1/34

OTHER PUBLICATIONS

Anany et al. Biocontrol of Listeria monocytogenes and *Escherichia coli* O157:H7 in meat by using phages immobilized on modified cellulose membranes. Appl Environ Microbiol. Sep. 2011;77(18):6379-87.*

Rich et al. Properties of coatings on RFID p-Chips that support plasmonic fluorescence enhancement in bioassays. Anal Bioanal Chem. Nov. 2012;404(8):2223-31.*

Lee et al. Selective immobilization of fusion proteins on poly(hydroxyalkanoate) microbeads. Anal Chem. Sep. 1, 2005;77(17):5755-9.*

Jaeger et al. Substrate Specificities of Bacterial Polyhydroxyalkanoate Depolymerases and Lipases: Bacterial Lipases Hydrolyze Poly(v-Hydroxyalkanoates). Applied and Environmental Microbiology, Aug. 1995, vol. 61, No. 8, p. 3113-3118.*

Voros et al. Optical grating coupler biosensors. Biomaterials 23 (2002) 3699-3710.*

Lu and Collins. PNAS. vol. 104, No. 27, pp. 11197-11202. Dispersing biofilms with engineered enzymatic bacteriophage (Year: 2007).*

Sutherland et al. FEMS Microbiol Lett. Mar. 12, 2004;232(1):1-6. The interaction of phage and biofilms. (Year: 2004).*

Sandro Nalli et al: Metabolites From the Biodegradation of Di-Ester Plasticizers by Rhodococcus Rhodochrous; Science of the Total Environment; 366; 2006; p. 286-294.

Masahito Oda et al: Rapid Detection of *Escherichia coli* O157:H7 by Using Green Fluorescent Protein-Labeled PP01 Bacterophage; Applied and Environmental Microbiology, Jan. 2004; p. 527-534.

(Continued)

*Primary Examiner* — Michelle S Horning
(74) *Attorney, Agent, or Firm* — Anthony R. Lambert (57) ABSTRACT

A biosensor for detecting a microorganism in a sample includes a polymer matrix and an immobilized layer of bacteriophages on the surface of the polymer matrix, wherein interaction of the bacteriophage with the microorganism causes a detectable physicochemical change in the polymer matrix. A method of detecting a microorganism in a sample using the biosensor includes the steps of contacting the sample with the biosensor; allowing the bacteriophage to bind to the microorganism in the sample; and detecting a physicochemical change in the polymer matrix, the change being indicative of the presence of the microorganism.

14 Claims, 3 Drawing Sheets

(56) References Cited

OTHER PUBLICATIONS

Heather A. Pearson: Phage-Bacterium War on Polymeric Surfaces: Can Surface-Anchored Bacterophages Eliminate Microbial Infections?; American Chemical Society; Biomacromolecules; 2013, 14, p. 1257-1261.

Thomas E. Waddell et al: Construction of Mini-Tn10luxABcam/Ptac-ATS and Its Use for Developing a Bacteriophage That Transduces Bioluminescence to *Escherichia coli* O157:H7; FEMS Microbiology Letters 182; 2000, p. 285-289.

Yunqiao Pu et al: Ionic Liquid as a Green Solvent for Lignin; Journal of Wood Chemistry and Technology; 27; 2007; p. 23-33.

Hitesh Handa: Recognition of *Salmonella typhimurium* by Immobilized Phage P22 Monolayers; Surf Sci 2008; Apr. 1; 602(7); p. 1392-1400.

Cesar Rodriquez-Emmenegger et al. Poly(Hema) Brushes Emerging as a New Platform for Direct Detection of Food Pathogen in Milk Samples; Biosensors and Bioelectronics 26; 2011; p. 4545-4551.

Michael J. Rothrock et al: Quantification of Zoonotic Bacterial Pathogens Withiin Commercial Poultry Processing Water Samples Using Droplet Digital PCR; Advances in Mircrobiology, 2013; 3; p. 403-411.

B. B. Sauer et al: Temperture Modulated DSC Studies of Melting and Recrystallization in Polymers Exhibiting Multiple Endotherms; Polymer 41; 2000; p. 1099-1108.

Dominic Sauvageau et al: Relative Rates and Mechanisms of Biodegradation of Diester Plasticizers Mediated by Rhodococcus Rhodochrous; The Canadian Journal of Chemical Engineering; vol. 87; Jun. 2009; p. 499-506.

L. Savenkova et al: Mechanical Properties and Biodegradation Characteristics of PHB-Based Films; Process Biochemistry; 35; 2000; p. 573-579.

J. M.Schultz: Microstructural Aspects of Failure in Emicrystalline Polymers; Polymer Engineering and Science; Jul. 1984; vol. 24, No. 10; p. 770-785.

P. A. Homes: Applications of PHB-A Microbially Produced Biodegradable Thermoplastic; Phys Technol; vol. 16; 1985; p. 32-36.

Toxicological Profile for Chloroform; US Department of Health and Human Services; Public Health Service Agency for Toxic Substances and Disease Registry; Sep. 1997; p. 1-343.

Peter Durand Skottrup: Towards On-Site Pathogen Detection Using Antibody-Based Sensors; Biosensors and Bioelectronics 24; 2008; p. 339-348.

Larisa Smelyanski et al: Site Directed Biotinylation of Filamentous Phage Structural Proteins; Virology Journal, 2011; 8: 495; p. 1-9.

Mateusz Smietana et al: Detection of Bacteria Using Bacteriophages as Recognition Elements Immobilized on Long-Period Fiber Gratings; Opticas Express 7971; Apr. 2011; vol. 19; No. 9; p. 1-8.

R. G. Tardiff: Health Effects of Organics: Risk and Hazard Assessment of Ingested Chloroform; JSTOR; Jul. 1977 p. 658-661.

Chanchan Wang et al: Immobilization of Active Bactriophages on Polyhydroxyalkanoate Surfaces; ACS. Appl. Mater. Interfaces; 2016; 8; p. 1128-1138.

Chun Z. Yang et al: Most Plastic Products Release Estrogenic Estrogenic Chemicals; A Potential Health Problem Tha Can Be Solved; Environmental Health Perspectives; vol. 119; No. 7; Jul. 2011; p. 989-996.

Miri Yemini et al: Specific Electrochemical Phage Sensing for *Bacillus cereus* and *Mycobacterium smegmatis;* Bioelechem; 2006; p. 1-5.

Jian Yu: Kinetics and Mechanism of the Monomeric Products From Abiotic Hydrolysis of Poly [(R)-3-Hydroxybutyrate] Under Acidic and Alkaline Conditions; Polymer Degradation and Stability; 89; 2005; p. 289-299.

Manfred Zinn: Occurrence, Synthesis and Medical Application of Bacterial Polyhydroxyalkanoate; Advanced Drug Delivery Reviews; 53; 2001; p. 5-21.

B.L. Hurrell et al: A Wide-Angle X-Ray Scattering Study of the Ageing of Poly (Hydroxybutyrate); Journal of Materials Science; 33; 1998; p. 1709-1713.

Nancy Tawil et al: Strategies for the Immobilization of Bacteriophages on Gold Surfaces Monitored by Surface Plasmon Resonance and Surface Morphology; J. Phys. Chem. C; 2013; 117; p. 6686-6691.

Massimo Gazzano: X-Ray Investigation on Melt-Crystallized Bacterial Poly(3-Hydroxybutyrate); Macromol. Chem. Phys. 198, 1997; p. 71-80.

P. J. Barham: Nucleation Behaviour of Poly-3-Hydroxy-Butyrate; Journal of Materials Science 19; 1984; p. 3826-3834.

Martin J. Loessner: Construction of Luciferase Reporter Bacteriophage A511::luxAB for Rapid and Sensitive Detection of Viable Listeria Cells; Applied and Environmental Microbiology, Apr. 19969; p. 1133-1140.

S. Luo and A.N. Netravali: A Study of Physical and Mechanical Properties of Poly (Hydroxybutyrate-Co-Hydroxyvalerate) Duriing Composting; Polymer Degradation and Stability 80; 2003; p. 59-66.

Carole Le Berre: Acetic Acid; Encyclopedia of Industrial Chemistry; 2013; 1-34.

Sameer P. Nalawade et al: Supercritical Carbon Dioxide as a Green Solvent for Processing Melts; Processing Polymer Aspects and Applications; Prog. Polym. Sci. 31, 2006; p. 19-43.

Khalil Arshak et al.: Conducting Polymers and Their Applications to Biosensors: Emphasizing on Foodborne Pathogen Detection; IEEE Sensors Journal, vol. 9, No. 12, Dec. 2009; p. 1942-1951.

J.D. Driskell et al.: Emerging Technologies in Nanotechnology-Based Pathogen Detection; Clinical Microbiology Newsletter, 31:18, 2009; p. 137-144.

Rotem Edgar et al: High-Sensitivity Bacterial Detection Using Biotin-Tagged Phage and Quantum-Dot Nanocomplexes; PNAS; Mar. 28, 2006; vol. 103; p. 4841-4845.

Hanno C. Erythropel et al: Leaching of the Plasticizer Di(2-Ethylhexyl)Phthalate (DEHP) From Plastic Containers and the Question of Human Exposure; Appl Microbial Biotechnol; 2014; p. 9967-9981.

A. Singh et al: Immobilization of Bacteriophages on Gold Surfaces for the Specific Capture of Pathogens; Biosensors and Bioelectronics 24; 2009; p. 3645-3651.

Sunil K. Arya et al: Chemically Immobilized T4-Bacteriophage for Specific *Escherichia coli* Detection Using Surface Plasmon Resonance; Analyst; 2011; 136; p. 486-492.

Clifford P. Weisel et al: Ingestion, Inhalation, and Dermal Exposures to Chloroform and Trichloroethene Tap Water; Environmental Health Perspectives; vol. 104; No. 1; Jan. 1996; p. 48-51.

Evelina Fasano: Migration of Phthalates, Alkylphenois, Bisphenol A and DI92-Ethylhexyl) Adipate From Food Packaging; Food Control; 27; 2012; p. 132-138.

Andrey A. Filippov et al: Bacteriophages Against Biothreat Bacteria: Diagnostic, Environmental and Therapeutic Applications; Bioterrorism & Biodefense; 2013; 8 pages.

Liling Fu et al: Detection of Bacillus Anthracis Spores Using Phage-Immobilized Magnetostrictive Milli/Macro Cantilevers; IEEE Sensors Journal; vol. 11, No. 8; Aug. 2011; p. 1684-1691.

Takashi Funatsu et al: Rapid and Sensitive Detection Method of a Bacterium by Sing a GFP Reporter Phage; Microbiol, Immunol; 46(6), 2002; p. 365-369.

L. Gervais et al: Immobilization of Biotinylated Bacteriophages on Biosensor Surfaces; Science Direct; Sensors and Actuators B 125, 2007; p. 615-621.

Zeinab Hosseinidoust et al: Going Viral: Designing Bioactive Surfaces With Bacteriophage; Colloids end Surfaces B: Biointerfaces 2014; p. 1-16.

Shin Horikawa et al: Effects of Surface Functionalization on the Surface Phage Coverage and the Subsequent Performance of Phage-Immobilized Magnetoelastic Biosensors; Biosensors and Bioelectronics 26; 2011; p. 2361-2367.

John N. Housby et al: Phage Therapy; Drug Discovery Today; vol. 14; No. 11/12; Jun. 2009; p. 536-540.

Yu Ri Kang et al: Corrigendum; Measurement Science and Technology; 22; 2011; p. 1-11.

S. Luo and A.N. Netravali: A Study of Physical and Mechanical Properties of Poly(Hydroxybutyrate-Co-Hydroxyvalerate) Duriing Composting; Polymer Degradation and Stability 80; 2003; p. 59-66.

(56) References Cited

OTHER PUBLICATIONS

Sameer P. Nalawade et al: Supercritical Carbon Dioxide as a Green Solvent for Processing Polymer Melts; Processing Aspects and Applications; Prog. Polym. SGi. 31, 2006; p. 19-43.
Anany et al: Biocontrol of Listeria Monocytogenes and *Escherichia coli* O157:H7 in Meat by Sing Phages Immobilized on Modified Cellulose Membranes; Applied and Environmental Microbiology; Sep. 2011; p. 6379-6387.
Preetam Anbukarasu et al: Tuning the Properties of Polyhydroxybutyrate Films Using Acetic Acid Via Solvent Casting; Scientific Reports; 5:17884; DOI: 10:1038; p. 1-14.
Carlos R. Arza et al: Network Formation of Graphene Oxide in Poly (3-Hydroxybutyrate) Nanocomposites; European Polymer Journal 59; 2014; p. 262-269.
P.J. Barham et al; The Relationaship Between Microstructure and Mode of Fracture in Polyhydroxybutyrate Journal of Polymer Science; Polymer Physics Edition; vol. 24. 1986; p. 69-77.
Rebecca Cademartiri et al; Immobilization of Bacteriophages on Modified Silica Particles; Biomaterials 31; 2010; p. 1904-1910.
D.Z. Bucci et al: PHB Packaging for the Storage of Food Products; Polymer Testing 24; 2005; p. 564-571.
L. Burne et al: Development of PH Sensitive Films for Monitoring Spoilage Volatiles Released Into Packaged Fish Headspace; Irish Journal of Agricultural and Food Research; vol. 42; No. 1; Jun. 2003; p. 119-129.
P.J. Barham et al: Crystallization and Morphology of a Bacterial Thermoplastic: Poly-3-Hydroxybutyrate; Journal of Materials Science 19; 1984; p. 2781-2794.

\* cited by examiner

BACTERIOPHAGE-BASED BIOSENSOR FOR MICROBIAL DETECTION

CROSS-REFERENCE TO RELATED APPLICATIONS

This application claims the benefit under 35 USC 119(e) of U.S. provisional application No. 62/042,424 filed Aug. 27, 2014.

FIELD

The present invention relates to a biosensor for use in detection of microorganisms in a sample.

BACKGROUND

Current methods of monitoring food products for microorganisms are based on End Product Analysis and Hazard Analysis Critical Control Points ("HACCP"); however, such methods rely upon limited sampling, periodic observation of products moving along the supply chain, and lengthy analytical laboratory testing which often requires amplification of microorganisms before conducting the actual testing. Bacterial plating can take up to four days to yield results, requires extensive training and experience, and may lead to false positives. Immunoassays (e.g., ELISA) and genetic analyses (e.g., PCR) involve pre-incubation periods, lengthy processing times, costly equipment, trained personnel, and may lead to false positives due to the inability to distinguish between live and dead pathogens (Leonard et al., 2003).

To overcome such weaknesses, various technologies have since been developed, including digital PCR techniques which remain unproven (Rothrock et al., 2013); antibody-based assays which are expensive and require trained personnel (Skottrup et al., 2008); and nano-based technologies (Driskell et al., 2009). However, these methods rely on punctual sampling through HACCP practices and thus do not provide real-time monitoring.

Bacteriophages ("phages") are highly specific, nanometer-scale bacterial viruses that exist naturally in food. Phages are commonly found in meat products at concentrations as high as $10^8$/g (Abedon, 2008). Phage-based products have been approved as antibacterial agents to treat meat products in Europe and the United States (Housby et al., 2009). Phages require a host organism to reproduce. Their high specificity has stimulated investigation into their use in biosensors or diagnostic tools. One promising approach is to genetically modify a phage to express a reporter protein upon recognition and infection of the bacterial host; for example, reporter phages have been developed for the expression of luciferase which emits a bioluminescent signal or green fluorescent protein ((Koeris et al., 2015; Loessner et al., 1996; Rosenbloom et al., 2014; Waddell et al., 2000; Funatsu et al., 2002). Genetically modified phages have also been used in the Bacterial Ice Nucleation Diagnostic test for *Salmonellae* (Jay et al., 2005). Pathogens can thus be detected at concentrations as low as 10 cells/g in meat and cheese within twenty-four hours, demonstrating a significant time improvement over plaque assays, and feasibility for use in diagnostic applications (Gervais et al., 2007). However, these methods rely upon off-line sampling and suspension of phages in solutions. Immobilized phages have been used for pathogen recognition in biosensors but these have limitations including, for example, detection limits, power supply requirements, sampling limitations, and loss of signal upon host lysis (Byrne et al., 2003; Tawil et al., 2013).

Several inexpensive commercial sensors can be utilized to monitor the environmental conditions of consumer products during shipment including, for example, time-temperature indicators which change color in response to elevated temperatures (e.g., OnVu™ from BASF, Monitor Mark™ from 3M), and colorimetric systems indicative of oxygen exposure (e.g., Ageless Eye™, Oxysense™). Colorimetric systems for monitoring fish freshness involve basic amines generated as fish spoils in the headspace reacting with a pH sensitive dye embedded in a polymer matrix (Byrne et al., 2003). Colorimetric systems necessitate visual inspection by eye or reader of the transitions, requiring line-of-sight access to the indicator.

SUMMARY

The present invention relates to a biosensor for use in detection of microorganisms in a sample.

In one aspect, the invention comprises a biosensor for detecting a microorganism in a sample, the biosensor comprising a polymer matrix and an immobilized layer of bacteriophages on the surface of the polymer matrix.

In one embodiment, the bacteriophage comprises a native or genetically modified phage. In one embodiment, the bacteriophage comprises a reporter phage carrying a gene which may code for a polyhydroxyalkanoate (PHA) depolymerase, another enzyme, another protein or a short-chain peptide. The polymer matrix may comprise a material detectably responsive to the protein, enzyme or peptide. Examples of detectable responses include degradation, increase in porosity, change in color and other examples described in this application.

In one embodiment, the polymer matrix comprises at least one polymer. The polymer may be a homopolymer or a co-polymer. The polymer may be included in a composite material, which may be a composite of polymers. In one embodiment, the composite comprises a degradable polymer layer defining an optical grating or a porous polymer layer. In one embodiment, the composite comprises a polymer layer defining an optical grating or a top porous polymer layer, and a degradable polymer layer. In one embodiment, the degradable polymer and the non-degradable polymer form a mixture.

In one embodiment, the polymer matrix is loaded with a dye.

In one embodiment, the polymer matrix is loaded with a plurality of conducting particles, or formed as a substrate for a radio frequency identification (RFID) antenna, or a coating for an antenna of a RFID tag.

In one embodiment, the polymer matrix is patterned at the nano-, micro- or millimeter-scale, or a combination thereof, the polymer matrix being a pure polymer or a polymer blended with a non-degradable polymer or non-polymeric material.

In one embodiment, the polymer matrix comprises a degradable or non-degradable polymer. In one embodiment, the polymer matrix comprises polylactic acid, polyhydroxyalkanoate or polycaprolactone. Those skilled in the art would recognize that other degradable polymers would also be suitable.

In one embodiment, the polymer matrix is in the form of a free-standing film. In one embodiment, the polymer matrix is a coating on a carrier layer.

In another aspect, the invention comprises a method of detecting a microorganism in a sample, comprising the steps of:

(a) contacting the sample with the above biosensor;
(b) allowing the bacteriophage to bind to the microorganism in the sample; and
(c) detecting a physicochemical change in the polymer matrix, caused by interaction of the bacteriophage with the microorganism.

In one embodiment, the sample comprises a solid or liquid sample. In one embodiment, the microorganism comprises a bacterium. In one embodiment, the sample comprises a surface. In one embodiment, the microorganism is selected from *Escherichia, Enterobacter, Listeria, Yersinia, Salmonella, Shigella, Campylobacter, Staphylococcus, Clostridia, Vibrio, Aeromonas, Bacillus,* or *Pseudomonas*. Those skilled in the art would recognize that other bacteria could also be detected.

In one embodiment, the physicochemical change comprises a change in color, color intensity, translucence, diffraction, reflectance, size, shape, thickness, flexibility, mechanical property, conductivity or impedance. In one embodiment, the physicochemical change is visually detected or detected using an instrument, such as a microscope, a fluorometer, an impedence analyzer, a RFID reader, a network analyzer, a laser, a charged-coupled device, a camera, a four-point probe, a multimeter, or a spectrophotometer, or a combination thereof.

BRIEF DESCRIPTION OF THE DRAWINGS

The invention will now be described by way of an exemplary embodiment with reference to the accompanying simplified, diagrammatic, not-to-scale drawings:

FIG. 1, parts A-C, are schematic diagrams showing steps for detecting a microorganism using one embodiment of the present invention. Genetically modified bacteriophages immobilized on a polymer matrix (FIG. 1, part A) bind, infect, and replicate within a microorganism (FIG. 1, part B), expressing an enzyme which is released upon infection and interacts with the polymer matrix to impart a detectable change in property (FIG. 1, part C).

FIG. 3, parts A-B, show poly-3-hydroxy butyrate thin films. The control film lacked bacteriophage T4 resulting in absence of plaques over an agar lawn of *E. coli* (FIG. 3, part A), while the bacteriophage T4-immobilized film resulted in the formation of plaques (FIG. 3, part B).

DETAILED DESCRIPTION

When describing the present invention, all terms not defined herein have their common art-recognized meanings. To the extent that the following description is of a specific embodiment or a particular use of the invention, it is intended to be illustrative only, and not limiting of the claimed invention. The scope of the claims should not be limited by the preferred embodiments set forth in the examples, but should be given the broadest interpretation consistent with the description as a whole.

The present invention relates to a bacteriophage-based biosensor for use in detection of microorganisms in a sample. As used herein, the term "biosensor" means an analytical construct for the detection of a microorganism which combines a biological component with a physicochemical detector. The biosensor translates a specific bio-recognition event into a detectable change in property. In one embodiment, the biological component comprises a bacteriophage, and the physicochemical detector comprises a polymer matrix.

The biosensor comprises a single platform which functions as a sensor, amplifier, and transducer. As a sensor and amplifier, the biosensor is functionalized with bacteriophage to impart specificity of recognition for a microorganism, with the bacteriophage subsequently amplified in the infected microorganism to achieve high titers. As a transducer, the biosensor reacts to a compound produced or released due to the infection to generate a detectable change in property indicative of the presence of the microorganism.

Figure 1:
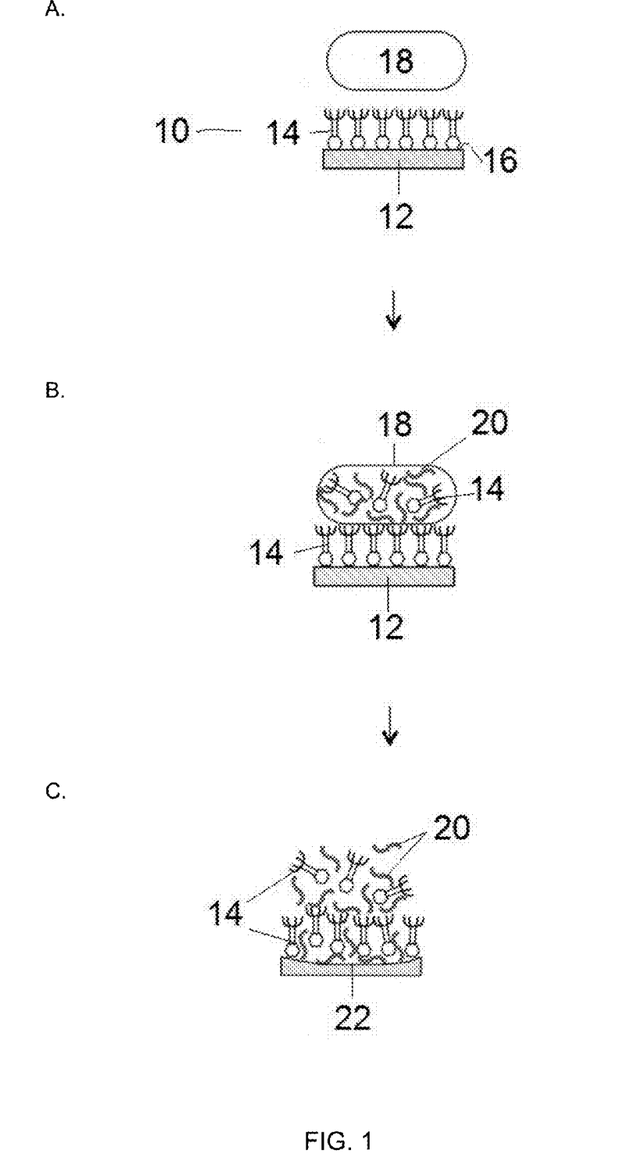

In one embodiment, the invention comprises a biosensor (10) which is generally shown in FIG. 1 to include a polymer matrix (12) and an immobilized layer of bacteriophages (14) on the surface (16) of the polymer matrix (12) for detection of a microorganism (18) in a sample.

In one embodiment, the invention comprises a method of detecting a microorganism in a sample, comprising the steps of:
(a) contacting the sample with the biosensor comprising a polymer matrix and an immobilized layer of bacteriophages on the surface of the polymer matrix;
(b) allowing the bacteriophage to bind to the microorganism in the sample; and
(c) detecting a physicochemical change in the polymer matrix caused by interaction of the bacteriophage with the microorganism.

As shown generally in FIG. 1, parts A-C, a sample which may contain a microorganism (18) is contacted with the biosensor (10). The sample may be applied to the biosensor (10), or the biosensor (10) may be applied to a surface to obtain a sample which may contain a microorganism (18). The bacteriophage (14) immobilized on the polymer matrix (12) binds, infects, and replicates within the microorganism (18) (FIG. 1, part B). A compound (20) is produced or released due to the infection to induce a physicochemical change (22) in the polymer matrix (12). The physicochemical change of the polymer matrix (12) to the compound (20) is detectable, indicating the presence of the microorganism (18) (FIG. 1, part C).

As used herein, the term "sample" means a sample which may contain a microorganism. A sample may comprise a solid or liquid sample including, but not limited to, meat, fish, dairy, water, and other products, or a bacterial culture of the sample. A sample may comprise a surface such as, for example, a laboratory benchtop, table, countertop, and the like, upon which a microorganism may be present. The invention may be used to provide either a "yes" or "no" result (i.e., the sample is either "positive" or "negative" for the microorganism), or a quantification of the prevalence of the microorganism. In one embodiment, the sample comprises a solid or liquid food sample. The invention provides selectivity and sensitivity with a short assay time, which are critical factors for food safety applications including for example, inspection of food products having short shelf times and low infection doses of pathogens; and monitoring the progress of sanitization or reconditioning of food products due to pathogenic contamination.

As used herein, the term "microorganism" means a bacterium including, but not limited to, *Escherichia, Enterobacter, Listeria, Yersinia, Salmonella, Shigella, Campylobacter, Staphylococcus, Clostridia, Vibrio, Aeromonas, Bacillus*, and *Pseudomonas*. In one embodiment, the microorganism comprises a foodborne bacterium.

As used herein, the term "bacteriophage" or "phage" means a virus which uses a bacterial host for replication and propagation of mature virions. The phage (14) binds to specific receptors on the surface of the microorganism (18). Such receptors include, but are not limited to, lipopolysaccharides, teichoic acids, proteins, flagella, and the like. The phage (14) then injects its DNA, and takes over the host machinery to propagate mature virions which may lyse the bacterium to infect a new host (in the lytic cycle), integrate its genome into the host DNA, remaining dormant until stimulated for replication and propagation (in the lysogenic cycle), or release virions without killing the host (for chronic infections).

The bacteriophage (14) may be native or genetically modified. In one embodiment, the bacteriophage (14) comprises wild-type T4 phage. In one embodiment, the bacteriophage (14) comprises a genetically modified phage. Suitable genetically modified phages include, but are not limited to, phages engineered to display peptides or proteins on their surface (i.e., phage display peptides, phage receptor binding proteins), and reporter phages.

In one embodiment, the bacteriophage (14) comprises a reporter phage. As used herein, the term "reporter phage" means a genetically modified phage used as a reporter gene carrier, to introduce a reporter gene of interest into the host microorganism upon infection. The reporter gene is expressed and codes for an enzyme, or a fluorescent protein or a colorimetric marker, which may be substrate dependent or independent, for subsequent microorganism detection.

Suitable reporter genes include, but are not limited to, those encoding fluorescent proteins, depolymerases, esterases, a protein or short-chain peptide, and the like (Loessner et al., 1996; Waddell et al., 2000; Oda et al., 2004). Those skilled in the art would recognize that other enzymes and proteins would also be suitable. In one embodiment, the reporter gene encodes a polyhydroxyalkanoate (PHA) depolymerase, such as PhaZCte. As used herein, the term "PhaZCte" means a PHA depolymerase naturally produced by *Comamonas testosteroni* and capable of hydrolyzing a PHA. As used herein, the term "PHA" means polyhydroxyalkanoate which is a natural biodegradable polyester. Standard molecular biology and genetic engineering techniques may be used to construct and insert a gene cassette into the desired bacteriophage (Loessner et al., 1996; Oda et al., 2004).

The bacteriophage (14) may be immobilized to the polymer matrix (12) by chemical bonding, physical adsorption, bulk mixing, or a combination thereof. More than one type of bacteriophage (14) may be immobilized to the polymer matrix (12) to enable identification and detection of multiple microorganism strains (18). Suitable methods for immobilization include, but are not limited to, biotinylation of the phage capsid for biotin-streptavidin affinity bonding (Gervais et al., 2007; Edgar et al., 2006; Smelyanski et al., 2011); direct covalent bonding using n-hydroxysulfosuccinimide and 1-ethyl-3-(3-dimethylaminopropyl) carbodiimide as linkers (Hermanson, 2008); and plasma-treated surface bonding (Pearson et al., 2013). Those skilled in the art would recognize that other phage immobilization methods would also be suitable.

Figure 3:
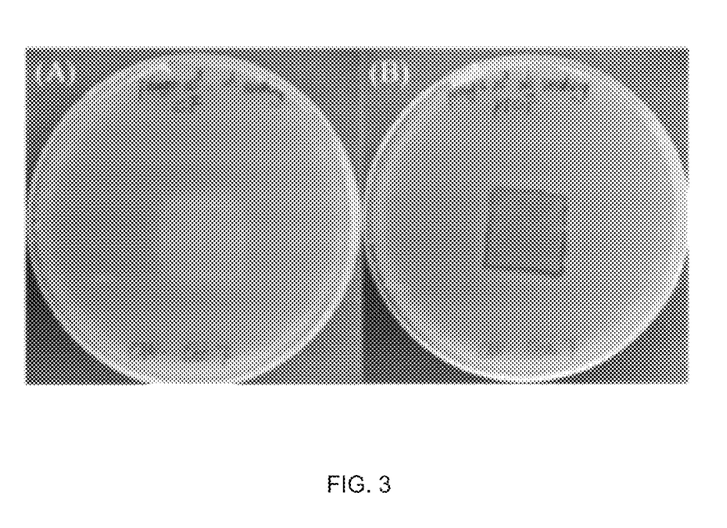

In one embodiment, modified plasma-treated surface bonding is used to immobilize bacteriophage (14) to the polymer matrix (12). In one embodiment, the biosensor (10) comprises a polymer matrix (12) comprising a poly-3-hydroxy butyrate ("PHB") film and bacteriophage T4 immobilized on the surface of the PHB film (FIG. 3, part B). A cell lysis region forms when the plasma-treated PHB film (i.e., having immobilized bacteriophage T4) is exposed to *E. coli* growing on an agar lawn (FIG. 3, part B). In contrast, no plaques form in the presence of the untreated control PHB film which lacked immobilized bacteriophage T4 (FIG. 3, part A).

It will be appreciated by those skilled in the art that the polymer matrix (12) may be immobilized with a virus other than a bacteriophage (14). Such viruses include, but are not limited to, a fungal virus or retrovirus for the detection of a fungus or cancer cell, respectively.

The compound (20) produced or released as a result of the infection of the microorganism (18) by the bacteriophage (14) induces a physicochemical change in the polymer matrix (12). Compounds (20) may include, but are not limited to, enzymes capable of degrading the polymer matrix (12) such as, for example, a depolymerase, an esterase, or another enzyme; a coded short-chain peptide; a biomolecule naturally released during the bacteriophage replication cycle such as, for example, a cell wall lysin; or a biomolecule released upon lysis of the microorganism.

As used herein, the term "polymer matrix" means a polymer which undergoes a physicochemical change in response to a compound produced or released by the infection of a microorganism by a phage. The polymer may be degradable or non-degradable. Suitable polymers include, but are not limited to, polylactic acid, polycaprolactones, PHA, PHB, and the like. In one embodiment, the polymer matrix (12) may comprise one polymer, or a combination of polymers.

Figure 2:
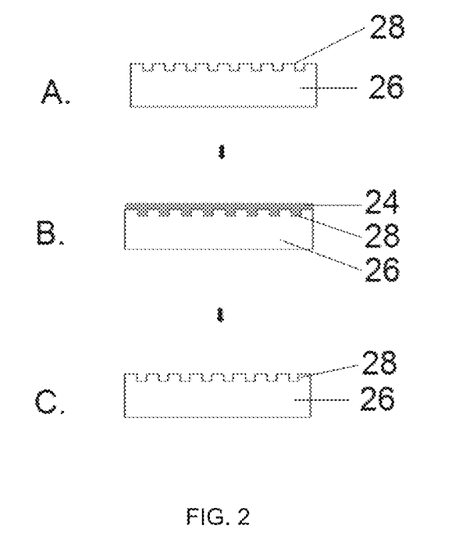
FIG. 2, parts A-C, are schematic diagrams showing steps for preparing one embodiment of the present invention comprising a bottom polymer layer defining an optical grating (FIG. 2, part A) being overlaid by a top polymer layer (FIG. 2, part B) which is degraded to expose the optical grating of the bottom polymer layer (FIG. 2, part C).
Figure 5:
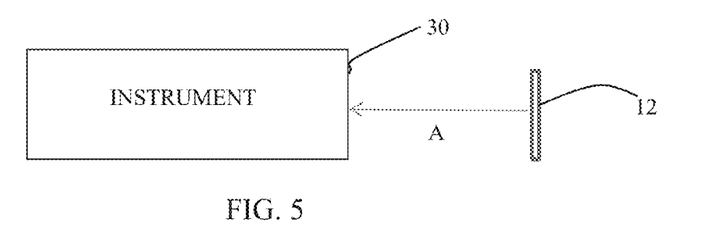
FIG. 5 shows an instrument for detecting a change in a polymer matrix.

In one embodiment, the polymer matrix (12) comprises a composite of polymers. In one embodiment, the polymer matrix (12) comprises two polymer layers (24, 26). One layer (24) comprises a degradable polymer. The other layer (26) comprises a polymer defining an optical grating (28) which is prepared by forming grooves on the surface of the polymer (FIG. 2, part A). The grating (28) is configured such that the wavelength of the light reflected is dependent on the structure of the grating (28). The degradable layer (24) is formed over the non-degradable layer (26) to mask the optical grating (28) using solvent casting or other suitable technique (FIG. 2, part B). When the degradable layer (24) is degraded, the optical grating (28) of the other layer (26) becomes exposed. The wavelength of reflected or transmitted light may be detected visually or using an instrument 30, such as a microscope, a laser, a charged-coupled device, a camera, or a spectrophotometer, or a combination thereof (FIG. 2, part C; FIG. 5).

In one embodiment, the polymer matrix (12) comprises PHB as the degradable polymer layer (24) and PDMS as the non-degradable polymer layer (26). PHB is degraded by PHB depolymerase within hours when the polymer matrix (12) is incubated in a liquid medium comprising PHB depolymerase. In one embodiment, the degradable polymer layer (24) and the non-degradable polymer layer (26) form an interpenetrating network that appears clear. When the degradable polymer layer (24) is degraded, the remaining porous network appears cloudy. It will be appreciated by those skilled in the art that other polymers could also be utilized.

The polymer matrix (12) can be patterned at the nano-, micro- or millimeter-scale, or a combination thereof. Such patterning confers a distinctive appearance to the polymer matrix (12) which may comprise a pure polymer or a polymer blended with a non-degradable polymer or non-polymeric material. Following interaction of the bacteriophage (14) with the microorganism (18), degradation of the patterned surface of the polymer matrix (12) may be observed by eye or detected using an instrument 30, such as a microscope, a fluorometer, an impedence analyzer, a RFID reader, a network analyzer, a laser, a charged-coupled device, a camera, a four-point probe, a multimeter, or a spectrophotometer, or a combination thereof. In FIG. 5, the arrow A represents for example, in various embodiments depending on the nature of the instrument, fluorescence, transmitted light or other transmitted electromagnetic radiation that has been modified by passage through the polymer matrix 12, reflected light or other reflected electromagnetic radiation, an electric current or other signal as required by the instrument being used.

In one embodiment, the top layer (24) comprises a degradable polymer, and the bottom layer (26) comprises a porous polymer. The top layer (24) is formed over the bottom layer (26) to mask the porosity. When the top layer (24) is degraded, the porosity of the bottom layer (26) becomes exposed. The change in porosity results in a change in appearance (for example, clear versus cloudy) that is visible by eye.

It will be appreciated by those skilled in the art that the composite may comprise the layers in the opposite orientation; for example, the composite may comprise a top polymer layer defining an optical grating or a top porous polymer layer, and a bottom degradable polymer layer. The composite could also comprise an interpenetrating network of two or more polymers.

In one embodiment, the polymer matrix (12) may be a free-standing film of polymer, a blend of polymers, or a composite material. This film may define an optical grating (28), be porous, be a homogeneous blend or be a heterogeneous mixture.

In one embodiment, the polymer matrix (12) is loaded with a dye which is released from the polymer matrix (12) following interaction of the bacteriophage (14) with the microorganism (18).

In one embodiment, the polymer matrix (12) is loaded with a plurality of conducting particles to form the antenna of a radio frequency identification (RFID) tag. The resonant frequency and/or reflected power of the antenna change as the polymer matrix (12) degrades. These changes in property can be remotely read using a RFID reader or network analyzer. In one embodiment, the polymer matrix (12) acts as a substrate for a RFID antenna. As the polymer matrix (12) degrades, the antenna is physically disrupted, undergoing an on-to-off transition. In one embodiment, the polymer matrix (12) is coated onto the antenna of a RFID tag. As the polymer matrix (12) degrades, it undergoes a change in dielectric properties that cause the reflected power and/or resonant frequency of the antenna to shift.

In one embodiment, the polymer matrix (12) can be coated onto a carrier layer in the form of a film or a coating.

Figure 4:
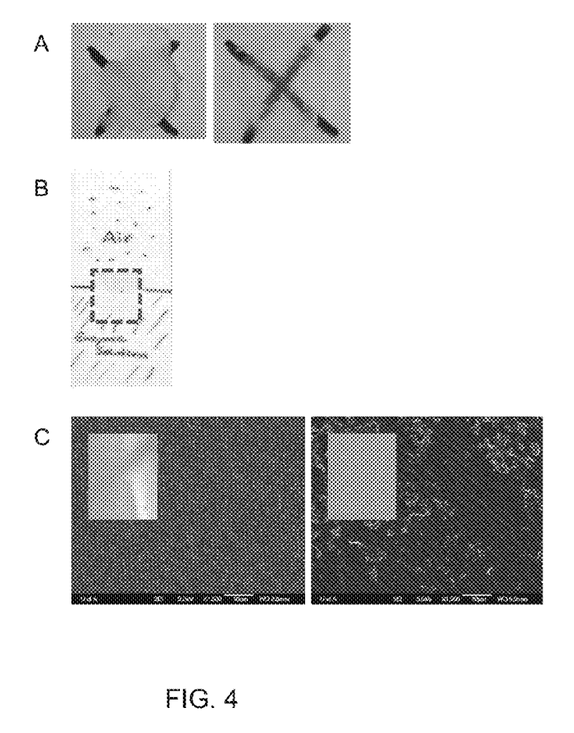
FIG. 4, parts A-C, show embodiments of physicochemical changes before and after the presence of microorganisms including a cloudy-to-clear change (FIG. 4, part A), loss of coloration by release of a dye (FIG. 4, part B), and degradation of a micro-patterned surface (FIG. 4, part C) as observed by SEM and visually (inset).

As used herein, the term "physicochemical change" means a change in the physical and/or chemical properties of the polymer matrix (12). Changes may include, but are not limited to, changes in color, color intensity, translucence, diffraction, reflectance, size, shape, thickness, flexibility, mechanical properties, conductivity and impedance. Changes may be readily observed or detected by a suitable detection device including, but not limited to, a microscope, a fluorometer, an impedence analyzer, a RFID reader, a network analyzer, a laser, a charged-coupled device, a camera, a four-point probe, a multimeter, or a spectrophotometer, or a combination thereof. FIG. 4, parts A-C, show various changes such as, for example, a cloudy-to-clear change (FIG. 4, part A), release of a colored dye (FIG. 4, part B), and degradation of a micro-patterned surface (FIG. 4, part C).

The biosensor (10) is relatively rapid, accurate and inexpensive due to the reduced minimum volume of sample required (i.e., microliters), inexpensive and disposable polymer material, and minimal testing steps (i.e., shorter run times). The polymer matrix (12) is passive, meaning it does not require a power source to undergo the physicochemical change. Since the physicochemical change occurs only upon infection of the microorganism (18) specifically targeted by the bacteriophage (14), false positives are avoided. Samples may be processed rapidly in minutes, compared to current time-consuming technologies which require a high degree of proficiency, extensive training and expensive equipment.

Commercial applications for the invention include, for example, detection of microorganisms in food or clinical samples; monitoring and quality control of food, beverage and agricultural products, environmental toxicology, and the like. For such applications, the biosensor (10) may be provided in the form of a label, packaging, sentinel package, test strip, swab test, or spray.

As will be apparent to those skilled in the art, various modifications, adaptations and variations of the foregoing specific disclosure can be made without departing from the scope of the invention claimed herein.

REFERENCES

The following references are incorporated herein by reference (where permitted) as if reproduced in their entirety. All references are indicative of the level of skill of those skilled in the art to which this invention pertains.

Abedon, S. T. (2008) Bacteriophage Ecology: Population Growth, Evolution, and Impact of Bacterial Viruses. Cambridge University Press.

Byrne, L., Lau, K. T. and Diamond, D. (June 2003) *Irish J. Agric. Food Res.* 42 (1):119-129.

Driskell, J. D. and Tripp, R. A. (September 2009) *Clin. Microbiol. Newsl.* 31 (18):137-144.

Edgar, R., McKinstry, M., Hwang, J., Oppenheim, A. B., Fekete, R. A., Giulian, G., Merril, C., Nagashima, K. and S. Adhya (2006) PNAS 103 (13):4841-4845.

Funatsu, T., Taniyama, T., Tajima, T., Tadakuma, H. and Namiki, H. (2002) *Microbiol. Immunol.* 46 (6):365-369.

Gervais, L., Gel, M., Allain, B., Tolba, M., Brovko, L., Zourob, M., Mandeville, R., Griffiths, M. and S. Evoy (August 2007) *Sens. Actuators B Chem.* 125 (2):615-621.

Hermanson, G. T. (2008) *Bioconjugate Techniques (2nd Edition)*, Academic Press, Waltham, Mass.

Housby, J. N. and N. H. Mann, N. H. (June 2009) *Drug Discov. Today* 14 (11-12):536-540.

Jay, J. M., Loessner, M. J. and Golden, D. A. (2005) Modern Food Microbiology. Springer. Leonard, P., Hearty, S., Brennan, J., Dunne, L., Quinn, J., Chakraborty, T. and O'Kennedy, R. (January 2003) *Enzyme Microb. Technol.* 32 (1):3-13.

Koeris, M. S., Thomason, J., Cappillino, M., Shivers, R. S., Brownell, D. R., Bowers, J. L., Lu, T. K. T., Krzymanska-Olejnik, E. Phage-Based Bacterial Detection Assay U.S. Ser. No. 14/309,389 (2015)

Loessner, M. J., Rees, C. E. D., Stewart, G. and Scherer, S. (April 1996) *Appl. Environ. Microbiol.* 62 (4):1133-1140.

Oda, M., Morita, M., Unno, H. and Y. Tanji (2004) *Appl. Environ. Microbiol.* 70:527-534. Pearson, H. A., Sahukhal, G. S., Elasri, M. O. and M. W. Urban (2013) *Biomacromolecules* 14:1257-1261.

Rosenbloom, M. J., Tekeian, E., and Koeris, M. S. System for On-Site Environmental Monitoring. U.S. Ser. No. 13/572,277 (2014)

Rothrock Jr., M. J., Hiett, K. L., Kiepper, B. H., Ingram, K. and Hinton, A. (2013) *Adv. Microbiol.* 3 (5):403-411.

Skottrup, P. D., Nicolaisen, M. and A. F. Justesen (November 2008) *Biosens. Bioelectron.* 24 (3):339-348.

Smelyanski, L. and J. M. Gershoni (2011) *Virol. J.* 8:495.

Tawil, N., E. Sacher, E., R. Mandeville, R. and M. Meunier (April 2013) *J. Phys. Chem. C.* 117 (13):6686-6691.

Waddell, T. E. and C. Poppe, C. (January 2000) *Fems Microbiol. Lett.* 182 (2):285-289.

What is claimed is:

1. A biosensor for detecting a microorganism in a sample, the biosensor comprising a polymer matrix and an immobilized layer of bacteriophages on the surface of the polymer matrix, wherein the bacteriophages comprise a phage carrying a reporter gene that codes for a depolymerase that is expressed when the phage infects the microorganism and the polymer matrix comprises a material detectably responsive to the depolymerase by degradation of the material.

2. The biosensor of claim 1, wherein the bacteriophage comprises a native or genetically modified phage.

3. The biosensor of claim 1, wherein the depolymerase is a polyhydroxyalkanoate (PHA) depolymerase.

4. The biosensor of claim 1, wherein the polymer matrix comprises at least one polymer, a blend of polymers, a co-polymer, or a composite material.

5. The biosensor of claim 4, wherein the composite comprises a degradable polymer and a non-degradable polymer.

6. The biosensor of claim 4, wherein the polymer matrix defines an optical grating.

7. The biosensor of claim 4, wherein the polymer matrix comprises a porous material.

8. The biosensor of claim 4, wherein the polymer matrix comprises a material that becomes porous upon exposure to a degradation-inducing substance.

9. The biosensor of claim 4, wherein the polymer matrix is loaded with a dye.

10. The biosensor of claim 4, wherein the polymer matrix is loaded with a plurality of conducting particles, or formed as a substrate for a radio frequency identification (RFID) antenna, or a coating for an antenna of a RFID tag.

11. The biosensor of claim 4, where the polymer matrix is patterned at the nano-, micro- or millimeter-scale, or a combination thereof, the polymer matrix being a pure polymer, a co-polymer, or a polymer blended with a non-degradable polymer or non-polymeric material.

12. The biosensor of claim 1, wherein the degradable material is selected from polylactic acid, polyhydroxyalkanoate, polycaprolactone.

13. The biosensor of claim 4, wherein the polymer matrix is in the form of a free-standing film or coating on a carrier layer.

14. A method of detecting a microorganism in a sample, comprising the steps of:
(a) contacting the sample with the biosensor of claim 1;
(b) allowing bacteriophage to bind to the microorganism in the sample; and
(c) detecting a physicochemical change in the polymer matrix caused by interaction of the bacteriophage with the microorganism.

* * * * *